United States Patent [19]

Myerowitz

[11] Patent Number: 5,217,865
[45] Date of Patent: Jun. 8, 1993

[54] SCREENING FOR TAY-SACHS DISEASE WITH CLONED DNA FOR BETA-HEXOSAMINIDASE

[75] Inventor: Rachel Myerowitz, Bethesda, Md.

[73] Assignee: The United States of America as represented by the Department of Health and Human Services, Washington, D.C.

[21] Appl. No.: 264,976

[22] Filed: Oct. 31, 1988

Related U.S. Application Data

[63] Continuation-in-part of Ser. No. 889,502, Jul. 25, 1986, abandoned.

[51] Int. Cl.⁵ ............................................. C12Q 1/68
[52] U.S. Cl. .................................... 435/6; 435/69.3; 435/91; 435/172.1; 435/172.3; 435/810; 435/975; 514/44; 436/501; 436/811; 536/23.2; 536/24.31; 536/24.33; 935/6; 935/17; 935/78; 935/88
[58] Field of Search ............... 435/6, 91, 172.1, 172.3, 435/810, 975, 69.3; 436/501, 811; 536/27; 514/44; 935/6, 17, 78, 88

[56] References Cited

PUBLICATIONS

Arpaia et al., "Identification of an altered . . . ", vol. 333, May 5, 1988 pp. 85-86, Nature.
Mullis et al., "Specific Synthesis of DNA . . . ", Methods in Enz., vol. 155, pp. 335-350, (1987).
Saiki et al, "Enzymatic Amplification of β-Globin . . . ", Science, vol. 230, pp. 1350-1354 (1985).
Myerowitz et al., "Human β-hexosaminidase α chain: . . ." PNAS, vol. 82 pp. 7830-7834, 1985.
Korneluk et al., "Isolation of cDNA clones . . . ", vol. 261, No. 18 (1986) (Jun. 25) pp. 8407-8413, J. of Biol. Chem.
Myerowitz et al., "cDNA clone for the α-chain . . . " PNAS vol. 81, pp. 5394-5398 (1984).
Myerowitz et al., "The Major Defect in Ashkenazi . . . ", The Journal of Biol. Chem., vol. 263, No. 35, pp. 18581-18589 (Dec. 15, 1988).
Ohno et al., "Molecular Genetic Heterogeneity in β Hex . . . ", vol. 22 (supplement), Neuroscience, pp. 5104 (1987).
Nakano et al., "A Point Mutation in the Coding Sequence . . . ", Journal of Neurochemistry, vol. 51 No. 3, 1988 (984-987).
Myerowitz et al., "Different Mutations in Ashkenazi . . . ", Science, vol. 232 pp. 1646-1648 (1986).
Ohno et al., "Classical Tay-Sachs Disease . . . ", J. Neurochem, vol. 48 (suppl) (p. 56) (1987).
Ohno et al, "Multiple Abnormal β-Hex . . . ", J. of Biol Chem, vol. 263, No. 34 (Dec. 5, 1988).
Andermann et al. in Tay-Sachs Disease: Screening and Prevention (publ. Alan R. Liss Inc., New York, N.Y., 1977) pp. 161-187.
Myerowitz (1988) Proc. Natl. Acad Sci (USA), vol. 85, pp. 3955-3959.
Ohno et al. (1988) Biochem. and Biophys. Res. Comm., vol. 153, No. 1, pp. 463-469.

Primary Examiner—Margaret Moskowitz
Assistant Examiner—Ardin H. Marschel
Attorney, Agent, or Firm—Cushman, Darby & Cushman

[57] ABSTRACT

Methods are disclosed of detecting mutations in the alpha chain gene that makes pre-natal diagnosis of Tay-Sachs disease possible. Screening for carrier heterozygotes of Tay-Sachs is made feasible by this invention.

6 Claims, 9 Drawing Sheets

```
-168            AGC CTC AGG TCC AGG CCG GAA GTG
            AAA GGG CAG GGT GTG GGT CCT CCT GGG
            GTC GCA GGC GCA GAG CCG CCT CTG GTC    -91

-90        ACG TGA TTC GCC GAT AAG TCA CGG GGG
            CGC CGC TCA CCT GAC CAG GGT CTC ACG
            TGG CCA GCC CCC TCC GAG AGG GGA GAC    -1
            CAG CGG GCC

1        ATG ACA AGC TCC AGG CTT TGG TTT TCG
   1        MET Thr Ser Ser Arg Leu Trp Phe Ser
            CTG CTG CTG GCG GCA GCG TTC GCA GGA
            Leu Leu Leu Ala Ala Ala Phe Ala Gly
            CGG GCG ACG GCC CTC TGG CCC TGG CCT
            Arg Ala Thr Ala Leu Trp Pro Trp Pro
            CAG AAC TTC                             90
            Gln Asn Phe                             30

91        CAA ACC TCC GAC CAG CGC TAC GTC CTT
  31        Gln Thr Ser Asp Gln Arg Tyr Val Leu
            TAC CCG AAC AAC TTT CAA TTC CAG TAC
            Tyr Pro Asn Asn Phe Gln Phe Gln Tyr
            GAT GTC AGC TCG GCC GCG CAG CCC GGC
            Asp Val Ser Ser Ala Ala Gln Pro Gly
            TGC TCA GTC                            180
            Cys Ser Val                             60

181        CTC GAC GAG GCC TTC CAG CGC TAT CGT
  61        Leu Asp Glu Ala Phe Gln Arg Tyr Arg
            GAC CTG CTT TTC GGT TCC GGG TCT TGG
            Asp Leu Leu Phe Gly Ser Gly Ser Trp
            CCC CGT CCT TAC CTC ACA GGG AAA CGG
            Pro Arg Pro Tyr Leu Thr Gly Lys Arg
            CAT ACA CTG                            270
            His Thr Leu                             90

271        GAG AAG AAT GTG TTG GTT GTC TCT GTA
  91        Glu Lys Asn Val Leu Val Val Ser Val
            GTC ACA CCT GGA TGT AAC CAG CTT CCT
            Val Thr Pro Gly Cys Asn Gln Leu Pro
            ACT TTG GAG TCA GTG GAG AAT TAT ACC
            Thr Leu Glu Ser Val Glu Asn Tyr Thr
            CTG ACC ATA                            360
            Leu Thr Ile                            120
```

FIG. 2B

```
361     AAT GAT GAC CAG TGT TTA CTC CTC TCT
121     Asn Asp Asp Gln Cys Leu Leu Leu Ser
        GAG ACT GTC TGG GGA GCT CTC CGA GGT
        Glu Thr Val Trp Gly Ala Leu Arg Gly
        CTG GAG ACT TTT AGC CAG CTT GTT TGG
        Leu Glu Thr Phe Ser Gln Leu Val Trp
        AAA TCT GCT                                     450
        Lys Ser Ala                                     150

451     GAG GGC ACA TTC TTT ATC AAC AAG ACT
151     Glu Gly Thr Phe Phe Ile Asn Lys Thr
        GAG ATT GAG GAC TTT CCC CGC TTT CCT
        Glu Ile Glu Asp Phe Pro Arg Phe Pro
        CAC CGG GGC TTG CTG TTG GAT ACA TCT
        His Arg Gly Leu Leu Leu Asp Thr Ser
        CGC CAT TAC                                     540
        Arg His Tyr                                     180

541     CTG CCA CTC TCT AGC ATC CTG GAC ACT
181     Leu Pro Leu Ser Ser Ile Leu Asp Thr
        CTG GAT GTC ATG GCG TAC AAT AAA TTG
        Leu Asp Val MET Ala Tyr Asn Lys Leu
        AAC GTG TTC CAC TGG CAT CTG GTA GAT
        Asn Val Phe His Trp His Leu Val Asp
        GAT CCT TCC                                     630
        Asp Pro Ser                                     210

631     TTC CCA TAT GAG AGC TTC ACT TTT CCA
211     Phe Pro Tyr Glu Ser Phe Thr Phe Pro
        GAG CTC ATG AGA AAG GGG TCC TAC AAC
        Glu Leu MET Arg Lys Gly Ser Tyr Asn
        CCT GTC ACC CAC ATC TAC ACA GCA CAG
        Pro Val Thr His Ile Tyr Thr Ala Gln
        GAT GTG AAG                                     720
        Asp Val Lys                                     240

721     GAG GTC ATT GAA TAC GCA CGG CTC CGG
241     Glu Val Ile Glu Tyr Ala Arg Leu Arg
        GGT ATC CGT GTG CTT GCA GAG TTT GAC
        Gly Ile Arg Val Leu Ala Glu Phe Asp
        ACT CCT GGC CAC ACT TTG TCC TGG GGA
        Thr Pro Gly His Thr Leu Ser Trp Gly
        CCA GGT ATC                                     810
        Pro Gly Ile                                     270
```

FIG. 2C

```
811      CCT GGA TTA CTG ACT CCT TGC TAC TCT
271      Pro Gly Leu Leu Thr Pro Cys Tyr Ser
         GGG TCT GAG CCC TCT GGC ACC TTT GGA
         Gly Ser Glu Pro Ser Gly Thr Phe Gly
         CCA GTG AAT CCC AGT CTC AAT AAT ACC
         Pro Val Asn Pro Ser Leu Asn Asn Thr
         TAT GAG TTC                                900
         Tyr Glu Phe                                300

901      ATG AGC ACA TTC TTC TTA GAA GTC AGC
301      MET Ser Thr Phe Phe Leu Glu Val Ser
         TCT GTC TTC CCA GAT TTT TAT CTT CAT
         Ser Val Phe Pro Asp Phe Tyr Leu His
         CTT GGA GGA GAT GAG GTT GAT TTC ACC
         Leu Gly Gly Asp Glu Val Asp Phe Thr
         TGC TGG AAG                                990
         Cys Trp Lys                                330

991      TCC AAC CCA GAG ATC CAG GAC TTT ATG
331      Ser Asn Pro Glu Ile Gln Asp Phe MET
         AGG AAG AAA GGC TTC GGT GAG GAC TTC
         Arg Lys Lys Gly Phe Gly Glu Asp Phe
         AAG CAG CTG GAG TCC TTC TAC ATC CAG
         Lys Gln Leu Glu Ser Phe Tyr Ile Gln
         ACG CTG CTG                                1080
         Thr Leu Leu                                360

1081     GAC ATC GTC TCT TCT TAT GGC AAG GGC
361      Asp Ile Val Ser Ser Tyr Gly Lys Gly
         TAT GTG GTG TGG CAG GAG GTG TTT GAT
         Tyr Val Val Trp Gln Glu Val Phe Asp
         AAT AAA GTA AAG ATT CAG CCA GAC ACA
         Asn Lys Val Lys Ile Gln Pro Asp Thr
         ATC ATA CAG                                1170
         Ile Ile Gln                                390

1171     GTG TGG CGA GAG GAT ATT CCA GTG AAC
391      Val Trp Arg Glu Asp Ile Pro Val Asn
         TAT ATG AAG GAG CTG GAA CTG GTC ACC
         Tyr MET Lys Glu Leu Glu Leu Val Thr
         AAG GCC GGC TTC CGG GCC CTT CTC TCT
         Lys Ala Gly Phe Arg Ala Leu Leu Ser
         GCC CCC TGG                                1260
         Ala Pro Trp                                420
```

FIG. 2D

```
1261        TAC CTG AAC CGT ATA TCC TAT GGC CCT
 421        Tyr Leu Asn Arg Ile Ser Tyr Gly Pro
            GAC TGG AAG GAT TTC TAC GTA GTG GAA
            Asp Trp Lys Asp Phe Tyr Val Val Glu
            CCC CTG GCA TTT GAA GGT ACC CCT GAG
            Pro Leu Ala Phe Glu Gly Thr Pro Glu
            CAG AAG GCT                                 1350
            Gln Lys Ala                                  450

1351        CTG GTG ATT GGT GGA GAG GCT TGT ATG
 451        Leu Val Ile Gly Gly Glu Ala Cys MET
            TGG GGA GAA TAT GTG GAC AAC ACA AAC
            Trp Gly Glu Tyr Val Asp Asn Thr Asn
            CTG GTC CCC AGG CTC TGG CCC AGA GCA
            Leu Val Pro Arg Leu Trp Pro Arg Ala
            GGG GCT GTT                                 1440
            Gly Ala Val                                  480

1441        GCC GAA AGG CTG TGG AGC AAC AAG TTG
 481        Ala Glu Arg Leu Trp Ser Asn Lys Leu
            ACA TCT GAC CTG ACA TTT GCC TAT GAA
            Thr Ser Asp Leu Thr Phe Ala Tyr Glu
            CGT TTG TCA CAC TTC CGC TGT GAG TTG
            Arg Leu Ser His Phe Arg Cys Glu Leu
            CTG AGG CGA                                 1530
            Leu Arg Arg                                  510

1531        GGT GTC CAG GCC CAA CCC CTC AAT GTA
 511        Gly Val Gln Ala Gln Pro Leu Asn Val
            GGC TTC TGT GAG CAG GAG TTT GAA CAG
            Gly Phe Cys Glu Gln Glu Phe Glu Gln
            ACC TGA GCC CCA GGC ACC GAG GAG GGT
            Thr ***                                     1620
            GCT GGC TGT                                  529

1621        AGG TGA ATG GTA GTG GAG CCA GGC TTC
            CAC TGC ATC CTG GCC AGG GGA CGG AGC
            CCC TTG CCT TCG TGC CCC TTG CCT GCG
            TGC CCC TGT                                 1710
```

FIG. 2E

```
1711    GCT TGG AGA GAA AGG GGC CGG TGC TGG
        CGC TCG CAT TCA ATA AAG AGT AAT GTG
        GCA TTT TTC TAT[AAT AAA CAT GGA TTA
        CCT GTG TTT                              1800

1801    AAA AAA AAA AGT GTG AAT GGC GTT AGG
        GTA AGG GCA CAG CCA GGC TGG AGT CAG
        TGT CTG CCC CTG AGG TCT TTT AAG TTG
        AGG GCT GGG                              1890

1891    AAT GAA ACC TAT AGC CTT TGT GCT GTT
        CTG CCT TGC CTG TGA GCT ATG TCA CTC
        CCC TCC CAC TCC TGA CCA TAT TCC AGA
        CAC CTG CCC                              1980

1981    TAA TCC TCA GCC TGC TCA CTT CAC TTC
        TGC ATT ATA TCT CCA AGG CGT TGG TAT
        ATG GAA AAA GAT GTA GGG GCT TGG AGG
        TGT TCT GGA                              2070

2071    CAG TGG GGA GGG CTC CAG ACC CAA CCT
        GGT CAC AAA AGA GCC TCT CCC CCA TGC
        ATA CTC ATC CAC CTC CCT CCC CTA GAG
        CTA TTC TCC                              2160

2161    TTT GGG TTT CTT GCT GCT GCA ATT TTA
        TAC AAC CAT TAT TTA AAT ATT ATT AAA
        CAC ATA TTG TTC TCT]                     2229
```

FIG. 5

| Mutant Probe | Normal Probe | |
|---|---|---|
| | ● | 90 |
| | ● | S.W. |
| ● | ● | S.S. |
| ● | | R.B. |
| ● | ● | T.B. |
| ● | ● | B.B. |
| ● | ● | GM2968 |
| ● | ● | GM3052 |
| | ● | GM3051 |
| ● | ● | GM515 |
| | ● | Normal Clone |
| ● | | Mutant Clone |

SCREENING FOR TAY-SACHS DISEASE WITH CLONED DNA FOR BETA-HEXOSAMINIDASE

This is a continuation-in-part of U.S. patent application Ser. No. 889,502, filed Jul. 25, 1986, now abandoned.

BACKGROUND OF THE INVENTION

1. Technical Field

The present invention is related to the isolation and characterization of a cDNA clone containing the entire coding sequence for the alpha chain of beta-hexosaminidase. More particularly, the present invention is related to a method for either prenatal diagnosing or adult screening for a genetic defect which is associated with Tay-Sachs disease.

2. Description of the Background Art

Tay-Sachs disease is an inherited disorder caused by mutation in the alpha-chain of beta-hexosaminidase A, a lysosomal enzyme composed of two polypeptides designated the alpha and beta chains (Stanbury et al., 1983, Metabolic Basis of Inherited Disease, p. 945; Sandhoff et al., 1984, Neuropediatrics 15 Suppl., 85-92). Deficiency of beta-hexosaminidase A results in storage of its major substrate, $GM_2$ ganglioside. Progressive accumulation of substrate leads to the characteristic neurodegenerative changes of Tay-Sachs disease patients. The disease is heterogeneous displaying a wide range of severity and age of onset. An early onset and fatal form of the disorder referred to as "classic" Tay-Sachs disease has a ten fold higher gene frequency among Ashkenazi Jews than the general population. A less publicized group having a carrier frequency equal to that of Ashkenazi Jews is a population of non-Jewish French Canadians located in Eastern Quebec (Anderman et al., 1977 Prog. Clin. Biol. Res. 18:161). In terms of age-of-onset, clinical course and biochemical parameters, French Canadian patients are indistinguishable from Ashkenazi patients (Hechtman et al., 1983 Clin. Gen. 24:206).

Beta-Hexosaminidase is a lysosomal enzyme composed of two polypeptide chains, alpha and beta, encoded on different chromosomes. Association of these polypeptides, a prerequisite for catalytic activity, results in three isozymes. Of these, only the A isozyme (aB) is able to hydrolyze all known beta-hexosaminidase substrates (beta-N-acetylglucosaminides and beta-N-acetylgalactosaminides, as well as 6-sulfated beta-N-acetylglucosaminides). The β isozyme (ββ) is unable to hydrolyze $GM_2$ ganglioside and the sulfated substrates, whereas the S isozyme (αα) has little catalytic activity except toward the sulfated compounds (Stanbury et al., 1983, Metabolic Basis of Inherited Disease, p. 945; Sandhoff et al., 1984, Neuropediatrics, 15 Suppl., 85-92). Different specificities in substrate binding and hydrolysis have been recently proposed for the alpha and beta chains (Kytzia et al., J. Biol. Chem. 256:7568-7572, 1985).

The biosynthesis of beta-hexosaminidase follows that of a typical lysosomal enzyme (Hasilik et al., 1984, in Lysosomes in Biology and Pathology, 7:pp3-16). Synthesis occurs on membrane-bound polysomes and insertion into the endoplasmic reticulum is followed by cleavage of the signal sequence and glycosylation of the enzyme. In the Golgi apparatus, the lysosomal enzymes are selected from the melange of glycoproteins for phosphorylation of certain mannose residues to form the recognition marker for binding to phosphomannosyl receptor and subsequent transport to the lysosomes. Within the lysosome, beta-hexosaminidase undergoes proteolytic processing from precursor to mature form. Association of the alpha and beta chains occurs after phosphorylation and is therefore thought to take place in the Golgi apparatus (Proia et al, J. Biol. Chem. 259:3350-3354, 1984).

Mutations in the genes encoding the alpha or beta chain of beta-hexosaminidase result in Tay-Sachs or Sandhoff disease, respectively genetic disorders displaying both clinical and biochemical heterogeneity (Sandhoff et al., 1984, Neuropediatrics 15 Suppl., 85-92). The best known of these is the classic late-infantile form of Tay-Sachs disease that occurs among Jews of Ashkenazi origin. A recent study reported the isolation of a clone containing a cDNA fragment for the alpha chain of human beta-hexosaminidase and a deficiency of mRNA in Ashkenazi Tay-Sachs fibroblasts (Myerowitz et al., 1984, PNAS, USA, 81:5394). However, the isolation and characterization of a cDNA clone containing the entire coding sequence of the alpha chain of human beta-hexosaminidase, has not heretofore been achieved.

In order to detect the many different kinds of mutations in human alpha-chain beta-hexosaminidase genes in individuals clinically displaying Tay-Sachs disease, one must have the entire, full length cDNA. If not, one would miss those mutations occuring in that part of the gene for which there is no cDNA. For example, the French-Canadian mutation occurs at the 5'-end of the gene which the prior cDNA clone (Myerowitz et al. PNAS, 1984 supra) did not have. Therefore, it is quite evident that the prior clone would have never made it possible to detect and elucidate the nature of Tay-Sachs mutation, for example, in the non-Jewish French-Canadian population.

SUMMARY OF INVENTION

It is an object of the invention to provide a cDNA clone carrying the entire coding sequence for the alpha chain of beta-hexosaminidase (hereinafter beta-HA).

This invention includes methods for detecting either the splice junction mutation or the insertion mutation for Tay-Sachs disease in the Ashkenazi Jewish population.

It is another object of the present invention to provide a kit and a method for detecting mutation for Tay-Sach's disease in humans.

BRIEF DESCRIPTION OF DRAWINGS

FIG. 2 shows nucleotide and deduced amino acid sequence of the alpha chain of human beta-hexosaminidase. The nucleotide sequence and derived primary alpha-chain structure are composites obtained, as shown in FIG. 1 from clones pβHα−1, −2, −3 and −5 and show the 5'-untranslated region, the entire alpha-chain protein sequence, and the 3'- untranslated region. The nucleotides are numbered in the 5' to 3' direction, starting with the A of the ATG codon that encodes the initiator methionine; negative numbers refer to the 5'-untranslated region. Amino acids are numbered so that residue 1 is the initiator methionine. The three possible N-linked glycosylation sites are boxed, and the termination codon is indicated by ***. The polyadenylylation signal in the 3'-untranslated region is underlined. The sequence of the 3' extension (nucleotides 1777–2229) present on a second mRNA encoding the alpha chain, obtained from clone pβHα−4, is shown in brackets;

FIG. 5 shows an assay for the exon 11 insertion defect in various α-chain genotypes. Genomic DNA samples were assayed for the insertion defect as described in Experimental Procedures IMR 90 (normal), S.W., (Ashkenazi normal), S.S. (Ashkenazi obligate heterozygote carrier), R.B. (Ashkenazi with classic Tay-Sachs), B.B. (Ashkenazi obligate heterozygote, father of R.B.), T.B. (Ashkenazi obligate heterozygote, mother of R.B.), GM2968 (Ashkenazi with classic Tay-Sachs), GM3052 (Ashkenazi obligate heterozygote, mother of GM2968), GM3051 (Ashkenazi obligate heterozygote, father of GM2968), GM515 (Ashkenazi with classic Tay-Sachs). Exposure was for 2 hours.

DETAILED DESCRIPTION OF INVENTION

Figure 1:
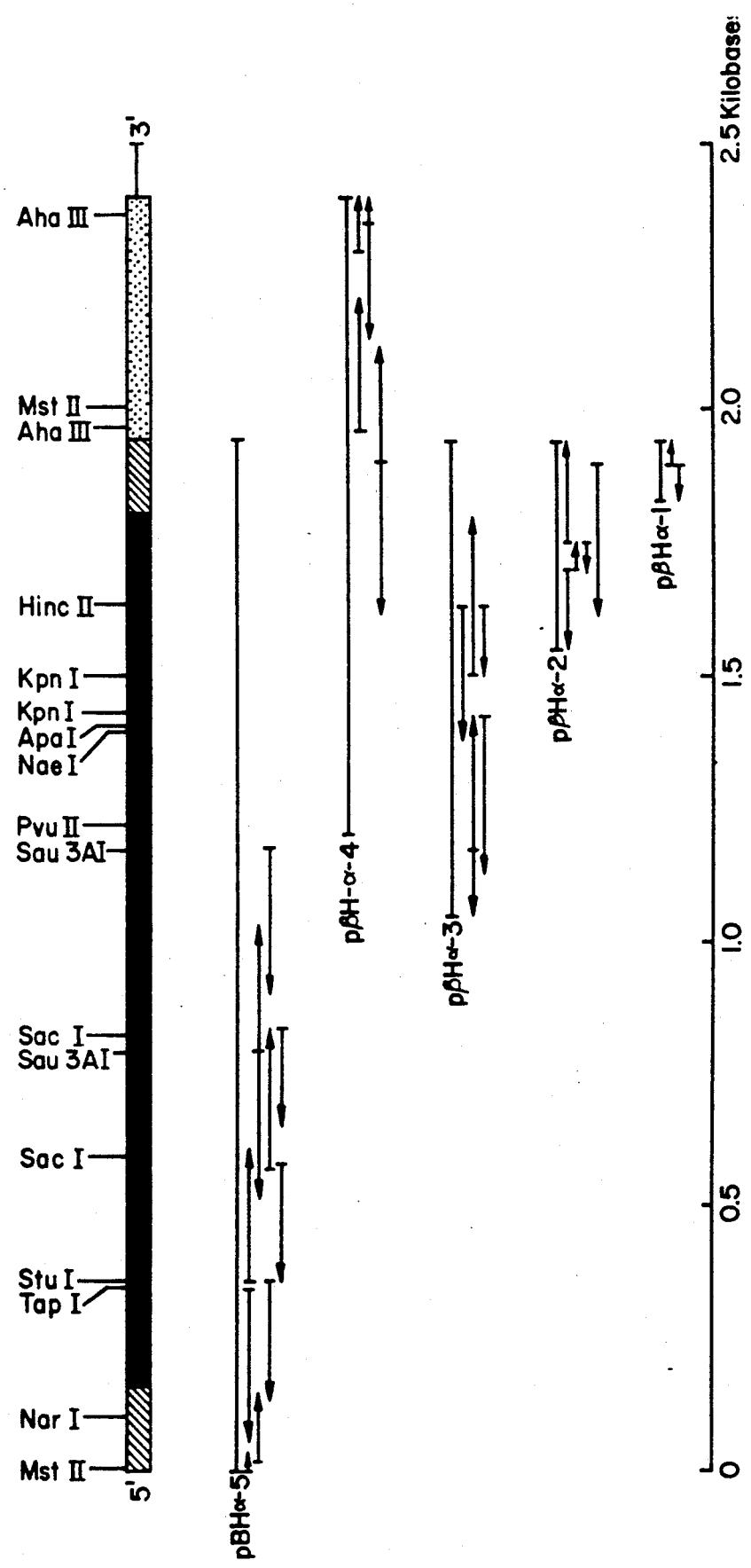
FIG. 1 represents the restriction map and sequencing strategy for obtaining the full sequence of cDNA for alpha-chain of beta-HA. The heavy black bar represents the coding region, the hatched bars designate the 5' and 3' untranslated regions, and the speckled bar represents the 3' extension present on a second mRNA encoding the alpha chain. The size [exclusive of poly(A) tail] and relationship of the cDNA inserts of pβHα−1, −2, −3, −4, and −5 are shown below the restriction map. The jagged line of pβHα−2 represents 37 bp coding for a region of an intron in the alpha-chain gene. Arrows below each cDNA insert show the direction and extent of DNA sequences.

The above and various other objects and advantages of the present invention are achieved by a clone of complimentary DNA (cDNA) carrying coding sequence for the entire alpha chain of beta-HA.

It is noted that unless defined otherwise, all technical or scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference.

MATERIALS AND METHODS

Determining who is a member of the Ashkenazi Jewish population and the non-Jewish French Canadian population located in Eastern Quebec can be achieved according to standard methodology. For instance, persons of Ashkenazi Jewish ancestry can be located by screening drives held at designated times and places. Radio announcements, flyers, notices posted in local synagogues, and similar advertising techniques may be employed to attract Ashkenazi Jews to the screening site. Blood samples taken from Ashkenazi Jew of childbearing age can be tested for Tay-Sachs using the methods of the present invention.

Similar methods can be used to screen for non-Jewish French Canadians of Eastern Quebec. Andermann et al, Prog. Clin. Biol. Res. 18:161 (1977) describes a method, whereby a number of families were studied from the north and south shores of the St. Lawrence River east of Quebec City. 650 individuals excluding obligate heterozygotes were tested, 618 in the extended kindreds of 4 of the Tay-Sachs families, and 32 in the Sandhoff families. Most of these samples were collected during 3 large field trips held at Ville Degelis on the road to New Brunswich (197 samples); in Arvida in the Lac St. Jean-Saguenay region (285 samples); and in Sayabec on the way to the Gaspe (125 samples). Each of these small towns is located at a distance of approximately 350 miles from Montreal. The remainder of the individuals tested were seen in the Montreal area, since they either live there or came to the hospital for the test.

The screening clinics were planned in advance, cooperation from the families, particularly the parents, being the most important factor in their organization. Letters were sent out to all members of the extended kindred living in the region several weeks prior to the clinic, informing them about the screening program and explaining the reasons why they should be tested. Local physicians and public health nurses also assisted in contacting family members and providing both professional and volunteer personnel. In at least one of the communities, the Marcus Welby television program on Tay-Sachs disease had been shown in French a short time earlier.

The screening clinics were usually held in a community center or church hall. For each individual tested, forms were filled with relevant identification and clinical data, as well as detailed pedigree linkage data, in order to identify the individual's position in the pedigree. The blood samples were immediately centrifuged, frozen, and transported to the laboratory in dry ice the following day.

The relevant identification and clinical data for each individual screened, including such variables as kindred number, relationship to proband, age, sex, diabetic status, pregnancy status, contraceptive pills, total hexosamindase, Hex A and B values, and carrier status were recorded onto a PDP-12 computer at the Montreal Neurological Hospital.

Materials. The adult human liver cDNA library was obtained from S. Orkin (Children's Hospital Medical Center, Boston, Mass. 02115). The simian virus 40-transformed human fibroblast cDNA library was obtained from H. Okayama (NIH, Bethesda, Md.). Radioisotopes and the Colony/Plaque Screen was obtained from New England Nuclear; HATF nitrocellulose filters was obtained from Millipore; NA-45 DEAE membranes was obtained from Schleicher & Schuell; oligo(dT) cellulose type 3 was obtained from Collaborative Research, Waltham, Mass.; restriction enzymes and T4 DNA ligase was obtained from Boehringer Mannheim; dideoxy- and deoxynucleotide triphosphates, M13 mp8, mp9, mp10, and mp11 cloning vectors were obtained from Pharmacia-PL Biochemicals.

Isolation of cDNA Clones. The adult human liver library (Prochownik et al., 1983, J. Biol. Chem. 258:8389-8394) was plated at a density of 8000 colonies per 150-mm plate on HAFT Millipore filters. A set of replicas was grown and transferred to chloramphenicol-containing plates (200 $\mu$g/ml) to amplify the plasmids. The colonies were lysed and processed by the method described by Hanahan et al., 1980, (Gene 10:63-67) and then hybridized with $^{32}$P-labeled cDNA insert of p$\beta$H$\alpha$-1 (2.5 ng/ml hybridization fluid) a cDNA insert encoding 119 base pairs (bp) of the 3' terminus of alpha-chain mRNA as described by Myerowitz et al 1984, supra. Three positive clones were obtained from 120,000 colonies screened. (Subsequent screenings of this and other libraries produced a similar frequency of positive clones.) These were rescreened at a density of 300 colonies per 100-mm plate. cDNA inserts were released from the vector by digestion with Pst I and their size was estimated by electrophoresis in a 1% agarose gel. Nucleotide sequence analysis of the longest clone, p$\beta$H$\alpha$-2, showed it to contain a 393-bp cDNA insert with a 3'-terminal sequence identical to the sequence of p$\beta$H$\alpha$-1 (FIG. 1). This insert was labeled with $^{32}$P and was used to screen a simian virus 40-transformed human fibroblast library (Okayama et al., 1983, Mol. Cell. Biol. 3:280-289). Screening of the library and analyses of the positive clones were similar to the procedure described above except that the library was plated on Colony/Plaque Screen and cDNA inserts were released from the vector by digestion with BamHI. The longest clone, p$\beta$H$\alpha$-3, isolated from this screen contained an 891-bp alpha-chain cDNA insert (FIG. 1). To enhance the probability of finding clones encoding the 5' region of the alpha chain, a 300=bp fragment (Pst I/Apa I; FIG. 1) was isolated from the 5' terminus of p$\beta$H$\alpha$-3 and used to reprobe the adult human liver library. Thus p$\beta$H$\alpha$-5 (FIG. 1), a clone containing the entire coding sequence for the alpha chain of human beta-hexosaminidase, was obtained. The 3' end of the cDNA insert of p8He-5 was found to be identical to p$\beta$H$\alpha$-3 by restriction enzyme mapping.

A deposit of the cDNA containing the entire coding sequence for the complete alpha-chain of beta-HA has been made in the American Type Culture Collection, Bethesda, Md., under accession number 67161. Upon issuance of a patent, this deposit shall continue to be maintained for at least 30 years or for the life of the patent and made available to the public without restriction, of course, consistent with the provisions of the law in this regard.

DNA Sequence Analysis. The sequence analysis of cDNA fragments was carried out by the Sanger dideoxy chain-termination method (Sanger et al., 1977, Proc. Natl. Acad. Sci. USA 74:5463-5467) with appropriate M13 vectors, the 17-mer sequencing primer, and $^{35}$S-labeled dATP (Biggin et al., 1983, Proc. Natl. Acad. Sci. USA 80:3963-3965).

Cell Culture. Fibroblasts from a cystic fibrosis patient (GM 1348), from Ashkenazi Jewish Tay-Sachs disease patient (GM 515) (Human Genetic Cell Repository, Institute for Medical Research, Camden, NJ), from a patient with Hurler syndrome (J.O.M.), and from non-Jewish French Canadian Tay-Sachs patients were grown as described by Sando et al., 1977, (Cell 12:619-627).

RNA Blot Hybridization. Poly(A)+ RNA from cultured human fibroblasts was electrophoresed in a 1% agarose/formaldehyde denaturing gel according to the procedure of Goldberg, 1980, (Proc. Natl. Acad. Sci. USA 77:5794-5798). Transfer of the RNA to Pall BI-ODYNE A transfer membrane (1.2 $\mu$m) (Pall, Glen Cove, N.Y.), hybridization with $^{32}$P-labeled probes, and washing of the blots were carried out as described by the manufacturer. Blots were exposed to Kodak x-ray film at $-70°$ C. using a Cronex Hi Plus intensifying screen.

Chromosomal Localization. Isolation and characterization of human-mouse cell hybrids has been known (Shows et al., 1984, Somat. Cell Mol. Genet. 10:315-318). The human chromosome content of these hybrids was determined by karyotyping (Shows et al., 1978, Cytogenet. Cell Genet. 21:99-104) and enzyme marker analysis (Shows et al., 1983, Adv. Hum. Genet. 2:341-452). High molecular weight DNA prepared from mouse, human, and hybrid lines was digested with Pst I, and the resulting fragments were electrophoretically separated in a 1% agarose gel. DNA was transferred to nitrocellulose filters (Maniatis et al., 1982, Molecular Cloning: A Laboratory Manual). The filters were hybridized with $^{32}$P-labeled p$\beta$H$\alpha$-2, washed, and exposed to the x-ray film as described (Maniatis, supra).

Computer Analysis. The nucleotide and amino acid sequences of the beta-hexosaminidase alpha chain and those of other lysosomal enzymes available in the literature were compared by the NUCLAN and PRTALN programs of Wilbur and Lipman (Proc. Natl. Acad. Sci. USA 80:726-730, 1983) and the significance of similarities was evaluated by the RDF program of Lipman and Pearson (Science 227;1435-1441, 1985).

Sequence Analysis of alpha-Chain cDNA Clones. The nucleotide sequence of the alpha-chain beta-hexosaminidase cDNA from the 5' -untranslated region to the poly(A) tail and the deduced amino acid sequence of the alpha-chain polypeptide are shown in FIG. 2. The cDNA is 1944 bp long, containing a 168-bp 5'-untranslated region with an in-frame termination codon found at nucleotide −85 to −87. A polyadenylylation signal (AATAAA) 22 bp upstream from the poly(A) tail punctuates the 186 bp 3'-untranslated region. A methionine-encoding triplet initiates an open reading frame of 1587 bp corresponding to 529 amino acids (Mr, 60,697) ending with a stop codon (nucleotides 1588–1590). The amino terminus is rich in hydrophobic residues characteristic of signal sequences. Three possible N-linked glycosylation sites are identified (nucleotides 343–345, 469–471, 883–885).

Figure 3:
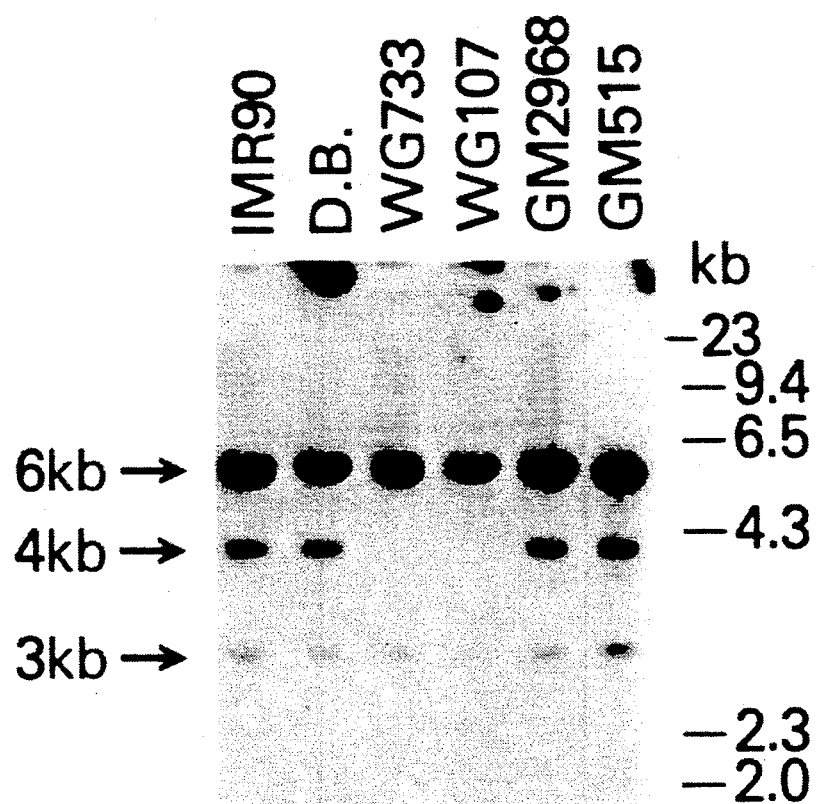
FIG. 3 shows Southern blot analysis of normal, French Canadian Tay-Sachs and Ashkenazi Tay-Sachs DNA. Normal (IMR90) and Ashkenazi Tay-Sachs (GM 515, GM 2968) fibroblast cultures were obtained from the Human Genetic Cell Repository, Institute for Medical Research, Camden, N.J. The non-Jewish French Canadian Tay-Sachs cells (WG 107, WG 733) were obtained from the Repository for Human Mutant Cell Strains, Montreal, Canada. DNA was isolated from these cultures as well as from whole blood leukocytes of a normal non-Canadian Ashkenazi individual (D.B.) who was not a heterozygote carrier for Tay-Sachs disease following standard procedures well known in the art. Genomic DNA of normals and mutants (7 μg) was digested to completion with EcoRI, fractionated on a 1% agarose gel and transferred to GeneScreen Plus (New England Nuclear Corp.) in 10×SSC. Transferred DNA was then hybridized at 42° in the presence of formamide to the insert of pβHα−5, a cDNA clone that contains the entire coding sequence for the alpha-chain of human beta-hexosaminidase and that had been labeled with $^{32}P$ to a specific activity of $2\times10^9$ (count/min per μg of DNA) by the random primer method, all such methods being well known in the art. Blots were washed as suggested by the manufacturer and exposed for 36 h to x-ray film using a Cronex Hi Plus intensifying screen.

Results shown in FIG. 3 clearly establish that an identical restriction pattern is obtained for the normal controls and Ashkenazi Tay-Sachs samples comprising three DNA fragments with approximate sizes of 6, 4 and 3 kilobases (kb) However, the 4 kb DNA fragment was absent from the restriction pattern of the non-Jewish French Canadia Tay-Sachs samples. (A restriction pattern similar to normal controls was also observed with Ashkenazi samples digested with PstI, HindIII or KpnI.) These results indicate that the DNA from Ashkenazi patients did not show major alpha-chain gene alterations detectable by Southern blotting, while DNA from the Canadian patients displayed similar deletions of a portion of the alpha-chain gene.

The region deleted in the alpha-chain gene of the French Canadian Tay-Sachs samples was determined by analyzing a Southern blot of EcoRI digested normal and mutant DNA's which had been hybridized sequentially with 3' and 5' terminal alpha-chain cDNA probes prepared from pβHα−5. The 3' terminal cDNA probe (312 base pairs) hybridized to the 6 kb genomic DNA fragment in all of the samples identifying this fragment as the 3' end of the alpha-chain gene and demonstrating that the 3' end was intact in the French Canadian mutants. Rehybridization of this same blot with a 5' terminal alpha-chain probe (356 bp) elicited a band in the normal samples corresponding to the 4 kb DNA fragment, but failed to produce a signal in the French Canadian samples. These results mapped the 5' terminal of the alpha-chain gene to the 4 kb fragment in EcoRI digests and indicated that a 5' terminal region of this gene was deleted in French Canadian Tay-Sachs cell lines WG 107 and WG 733. This conclusion is supported by the results of an identical experiment performed with StuI digested normal and mutant DNA samples Hybridization with the 5' terminal alpha chain cDNA probe failed to produce a signal in the mutants but did so in the normals, (0.6 kb), while the 3' terminal probe produced a signal (4.6 kb) in both types of DNA samples.

The size of the alpha-chain gene deletion in the French Canadian Tay-Sachs patients was estimated by hybridizing normal and mutant DNA with probes obtained from normal alpha-chain genomic clones. Following Southern transfer, normal and mutant DNAs that had been digested with EcoRI were hybridized with a $^{32}$P labeled genomic probe (300 bp). This probe mapped 700 bp upstream from the 5' end of the 5' terminal alpha-chain cDNA probe and hybridized with DNA in the normal samples but failed to hybridize with DNA in the French Canadian samples indicating that the mutants lack DNA sequences functioning in the initiation of alpha-chain gene transcription as well as 5' exonic piece(s) since the 5' terminal cDNA probe was obtained from a cDNA clone of full length or no more than 50–100 bp short.

Figure 4A:
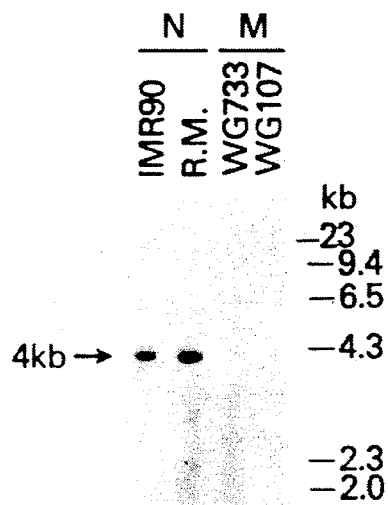
FIG. 4 shows the extent of the 5' terminal alpha-chain gene deletion in French Canadian Tay-Sachs Patients. Normal [IMR90, R.M. (an Ashkenazi Jewish non-Canadian subject who was not a heterozygote carrier for Tay-Sachs disease), D.B.] and French Canadian Tay-Sachs (WG 733, WG 107) DNA (10 μg/sample) was digested with EcoRI, fractionated on a 1% agarose gel, transferred to GeneScreen Plus and processed as described above except that the blots displayed in (B) and (C) were obtained by transfer in 0.4 M NaOH and 0.6 M NaCl. (A): Hybridization with a 300 bp DNA sequence obtained from an alpha-chain genomic clone and mapping 700 bp upstream from the 5' end of the 5' terminal cDNA probe. (B): Hybridization with a 600 bp alpha-chain intronic sequence obtained from an alpha-chain genomic clone and mapping 4.7 kb downstream from the 5' end of the 5' terminal alpha-chain cDNA probe. (C) Hybridization with a 300 bp alpha-chain intronic sequence obtained from an alpha-chain genomic clone and mapping 7.6 kb downstream from the 5' end of the 5' terminal cDNA probe. Exposure was for 48 hr. N=Normal and M=Mutant.
Figure 4B:
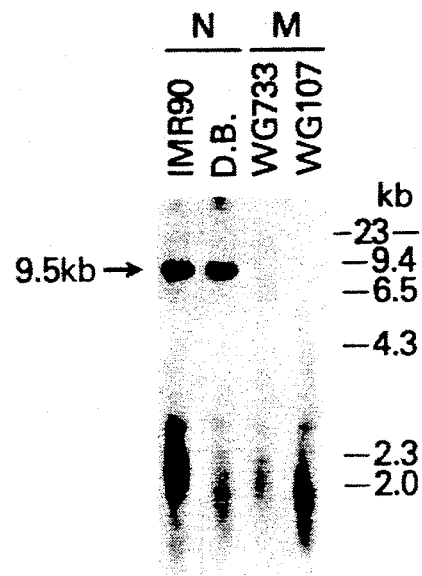
Figure 4C:
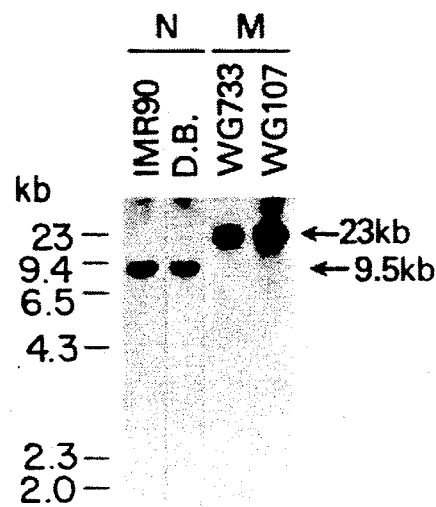

To delimit the 3' end of the deletion, normal and mutant DNA samples that had been digested with EcoRI and transferred to nylon-membranes were probed with two intronic portions of the α-chain gene. One intronic sequence (600 bp) mapping 4.7 kb downstream from the 5' end of the 5' terminal cDNA probe hybridized with the normal samples (9.5 kb band) but Yielded no signal in the mutants (FIG. 3, B). A second intronic sequence (300 bp) mapping 7.6 kb downstream from the 5' end of the 5' terminal cDNA probe hybridized to both normal (a 9.5 kb band) and mutant (23 kb band) DNA samples (FIG. 4, C). (Hybridization of this probe to DNA fragments of different sizes in the normals and mutants results from alterations in the EcoRI restriction pattern of the mutant as a consequence of the deletion.) These results indicated that the α-chain deletion in French Canadian Tay-Sachs mutants extended between 5.3 and 7.6 kb downstream from the 5' terminus of the a-chain cDNA, assuming a minimum requirement of a 50 bp hybridization for production of a signal.

Apart from the general utility of the full length α-chain cDNA of the present invention in characterizing the mutations in the beta-HA encodinq genes in individuals affected with Tay-Sachs disease the cDNA clone of the present invention can, also be readily used for prenatal diagnosis and heterozygote carrier screening of the French Canadian population which is a high risk group for this disorder. This is achieved as follows.

(a) First, isolate DNA from blood leucocytes of the person to be screened. In the case of a fetus isolate DNA from chronic villi. Include normal control DNA.

(b) Cleave the DNA with the restriction enzyme, such as EcoRI. In addition cleave DNA from a normal individual already determined not to be a Tay-Sachs carrier. Cleavage produces fragments of the genomic DNA of varying sizes.

(c) Electrophorese the cleaved λDNA samples (patients and normals) on a 1% agarose gel. This separates the cleaved DNA (i.e. DNA fragments) by size. Include size standards (such as Hind III cleaved DNA) on the gel.

(d) After electrophoresis is complete, transfer the fractionated DNA fragments of the samples (normal and patients and standards) onto a nylon membrane by the method of Southern, which is referred herein as a Southern blot.

(e) Hybridize the Souther blot with a $^{32}$P (isotope) labeled 300 bp piece of DNA which has been obtained from the normal alpha-chain gene. This piece of DNA maps 7.3 kilobases downstream from the 3' end of the first exon of the alpha-chain normal gene, hence forth called the "intron probe". This intron probe hybridizes (binds) with the DNA fragment of the normal or patient EcoRI cleaved DNA on the Southern blot which contains base pairs complementary to it. After hybridization, wash the Southern blot as described herein supra, to remove nonspecifically bound isotope ($^{32}$P) and expose the blot to x-ray film following standard techniques well known in the art. Remove x-ray film after 24 hours and observe the radiograph. Results similar to FIG. 4, particularly FIG. 4(c) would be observed indicating the following:

1) Normal will give one band at 9.5 kilobases;
2) Heterozygote carrier will give 2 bands, one at 9.5 and the other at 23 kilobases.
3) An affected fetus or individual will give one band at 23 kilobases.

Similarly a diagnostic test for Tay-Sachs disease in the Ashkenazi Jewish population is prepared from the identified mutation as follows.

1) Isolate DNA from blood leukocytes of any Ashkenazi Jewish person to be screened. In case of a fetus isolate DNA from chronic villi. Include normal control DNA.

2) Treat samples with an appropriate restriction enzyme and electrophorese on a 1% agarose gel. Transfer the fractionated DNA samples onto a nylon membrane according to the method of Southern (Southern blot). Make a duplicate blot of these samples.

3) Prepare a $^{32}$P labeled oligonucleotide probe (about 20 base pairs) which matches the sequence of the normal gene in the region of the mutation present in Ashkenazi Jewish Tay-Sachs patients (probe A). Prepare the same size probe which matches the analogous sequence in the mutant, that is catches the mutated base pair as well as the flanking regions (probe B).

4) Hybridize one Southern blot with probe A and the duplicate blot with probe B.

5) Results: Normal control DNA hybridized with probe A would form a stable hybrid and yield a signal whereas samples bearing the mutation would not yield a signal. This is due to the fact that a hybridization covering a short stretch of about 20 base pairs will be unstable with a single base pair mismatch.

6) Hybridization with probe B will yield the reverse results; the normal controls would form an unstable hybrid with this probe—that is no siqnal: but the mutants would.

7) Heterozygote carriers would form a stable hybrid with both probes.

A kit comprising a container containing the intact or fragmented cDNA of the present invention, either cryopreserved or otherwise, an oligonucleotide probe, an intron probe about 300 bp DNA and the like, including containers containing restriction enzymes and instructions to carry out the diagnostic and/or screening procedure as described herein is, of course, now made possible, conveniently put together and made available for clinical use in accordance with the present invention.

It is understood that the examples and embodiments described herein are for illustrative purposes only and that various modifications or changes in light thereof will be suggested to persons skilled in the art and are to be included within the spirit and purview of this application and the scope of the appended claims. The following examples use the methods and materials described above.

EXAMPLE 1

This example demonstrates a method for detecting a splice junction mutation for Tay-Sachs disease in the Ashkenazi Jewish population.

Genomic DNA isolated from cultured cells or blood was used (1 μg) as the template in the polymerase chain reaction to amplify a segment of DNA (117 bases) flanking the splice junction mutation. The reaction was carried out for 27 cycles utilizing two 23 base primers having the following sequences. PCA$_1$ has a sequence of 5'CCCCTGAGCAGAAGGCTCTGGTG3'. PCA$_2$ has a sequence of 5'TCCTGCTCTCAGGCCCAACCCTC3'.

These primers and Taq I polymerase along with a DNA amplification kit (sold by Gene Amp, Perkin Elmer Cetus) are used as described by the manufacturer's instructions with the exception that the unnealing step was performed at 55° C. Duplicate sets of samples (7- μl aliquots) were applied, denatured, and fixed to Biotrans membranes (0.2 μm) according to the DNA dot-blot protocol described by the manufacturer. Both sets of samples were prehybridized for 1 hour at 37° C. in 0.1% polyvinylpyrrolidone/0.1% Ficoll/0.1% bovine serum albumin/0.9 M sodium chloride. 0.05 M sodium phosphate, pH 8.3/0.005 M EDTA/500 μg of denatured salmon sperm DNA per ml. One set of samples was hybridized with a $^{32}$P-labeled 19 base oligomer complementary to the sense strand of the normal allele (5' C-A-G-G-C-T-C-T-G-G-T-A-A-G-G-G-T-T-T 3'), and the other set was hybridized with a 19-base oligomer complementary to the send strand of the mutant allele (5'C-A-G-G-C-T-C-T-G-C-T-A-A-G-G-G-T-T-T 3'). Filters were washed in 0.36 M sodium chloride/0.02 M sodium phosphate, pH 8.3/0.002 M EDTA for 15 minutes at 4° C., then for 30 minutes at ambient temperature, and finally for 2 minutes at 53° C. The ambient-temperature wash solution was 0.1% in NaDodSO$_4$. Filters were exposed to x-ray film in the presence of a Cronex Hi Plus intensifying screen for 2 hours.

EXAMPLE 2

This example demonstrates a method for detecting an insertion mutation for Tay-Sachs disease in the Ashkenazi Jewish population.

Amplification of specific genomic DNA sequences is first conducted. Genomic DNA, isolated from either cultured cells, whole blood, or leukocyte pellets, was used (1 μg) as the initial template in the polymerase chain reaction to amplify a segment of exon 11 encompassing the insertion defect. The reaction was carried out for 27 cycles utilizing two 23 base primers, (5'-GTGTGGCGAGAGGATATTCCAGT-3') and (5'-TTCAAATGCCAGGGGTTCCACTA-3').

A dot-blot assay for the α-chain insertion defect is then conducted. One-twentieth of each amplified DNA sample was applied in duplicate to a Biotrans nylon membrane (0.2 μ, ICN) denatured and fixed to the membrane according to the dot blot protocol supplied by the manufacturer. One set of samples was hybridized to mutant probe, (5'-GAACCGTATATCTATCCTA-3') with a sequence complementary to that found in mutant exon 11. The other set of samples was hybridized to normal probe, (5'-GAACCGTATATCCTATGGC-3') with a sequence complementary to that found in normal exon 11. Both probes were end labeled to a specific activity of $5 \times 10^8$ cpm/μg with [γ-P$^{3\ 2}$] ATP (6000 Ci/mmole). The blots were washed and exposed to x-ray film at −70° C. in the presence of a Cronex intensifying screen.

I claim:

1. A method of detecting a splice junction mutation in the alpha-chain gene coding for beta-hexosaminidase related to Tay-Sachs disease comprising the steps of:
(a) obtaining a sample of the DNA of a person or fetus to be tested;
(b) amplifying a 135 base pair sequence of genomic DNA encompassing a splice junction mutation by using two 23 base oligonucleotides PCA$_1$ and PCA 2 complementary to sequences flanking the alpha-chain mutation as primers in a polymerase chain reaction, said PCA$_1$ having a sequence of 5'-CCCCTGAGCAGAAGGCTCTGGTG-3' and said PCA$_2$ having a sequence of 5'-TCCTGCTCTCAGGCCCAACCCTC-3';

(c) denaturing and loading duplicate sets of samples into a dot blot manifold containing a nylon filter;

(d) hybridizing one set of samples with a first probe specific for the normal allele, said first probe having the sequence 5'-CAGGCTCTG-GTAAGGGTTT-3', and the other set with a second probe specific for the mutant allele, said second probe having the sequence 5'-CAGGCTCTG-CTAAGGGTTT-3';

(e) washing the blots to remove non-specifically bound probe; and (f) comparing radiograms to distinguish between normal DNA which hybridizes only with normal allel specific probe, DNA from heterozygote carriers which hybridizes with both normal and mutant specific probes, and DNA from affected individuals which hybridizes only with the mutant probe.

2. A method of detecting an insertion mutation in the alpha-chain gene coding for beta-hexosaminidase related to Tay-Sachs disease comprising the steps of:

(a) obtaining a sample DNA of a person or fetus to be tested;

(b) amplifying a 117 base pair sequence of genomic DNA encompassing an insertion mutation by using two 23 base primers, 5'-GTGTGGCGAGAG-GATATTCCAGT-3' and 5'-TTCAAATG-CCAGGGGTTCCACTA-3';

(c) denaturing and loading duplicate sets of samples into a dot blot manifold containing a nylon filter;

(d) hybridizing one set of samples with a first probe specific for the normal allele, said first probe having the sequence 5'-GAACCGTATATC-CTATGGC-3' and the other set with a second probe specific for the mutant allele, said second probe having the sequence 5'-GAACC-GTATATCTATCCTA-3';

(e) washing the blots to get rid of nonspecifically bound probe; and (f) comparing radiograms that will show that DNA from normal individuals hybridizes only with the normal allele specific probe while DNA from heterozygote carriers hybridize with both the normal and mutant specific probes, and DNA from affected individuals hybridizes only with the mutant probe.

3. A kit for detecting an insertion mutation for Tay-Sachs disease, wherein said mutation is of bases TATC in exon 11 of the gene encoding the alpha chain of beta hexosaminidase, said kit comprising a container containing cloned nucleic acid encoding the entire alpha chain of beta-hexosaminidase and instructions for carrying out a screening process for detecting the presence of said insertion mutation for Tay-Sachs disease utilizing said cloned nucleic acid.

4. The method according to claim 1, wherein said sample of DNA is taken from a member of the Ashkenazi Jewish population.

5. The method according to claim 1, wherein said sample of DNA is taken from a member of the French Canadian Eastern Quebec population.

6. The method according to claim 2, wherein said sample of DNA is taken from a member of the Ashkenazi Jewish population.

* * * * *